(12) United States Patent
Ito et al.

(10) Patent No.: US 12,294,779 B2
(45) Date of Patent: May 6, 2025

(54) IMAGING DEVICE, OCULAR MOVEMENT DATA PROCESSING SYSTEM, AND CONTROL METHOD

(71) Applicant: J. MORITA MFG. CORP., Kyoto (JP)

(72) Inventors: Yutaka Ito, Kyoto (JP); Fuyuki Yamada, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 76 days.

(21) Appl. No.: 17/735,597

(22) Filed: May 3, 2022

(65) Prior Publication Data

US 2022/0360706 A1    Nov. 10, 2022

(30) Foreign Application Priority Data

May 10, 2021   (JP) ................................ 2021-079598

(51) Int. Cl.
*H04N 23/611*     (2023.01)
*H04N 23/51*      (2023.01)
*H04N 23/661*     (2023.01)

(52) U.S. Cl.
CPC ........... *H04N 23/611* (2023.01); *H04N 23/51* (2023.01); *H04N 23/661* (2023.01)

(58) Field of Classification Search
CPC .... H04N 23/611; H04N 23/51; H04N 23/661; A61B 3/005; A61B 5/4863; A61B 3/113
See application file for complete search history.

(56) References Cited

U.S. PATENT DOCUMENTS

| 6,003,991 A * | 12/1999 | Viirre ..................... A61B 3/145 348/E13.047 |
| 2003/0086061 A1 | 5/2003 | Pfleger |
| 2008/0192202 A1 | 8/2008 | Lewkowski |
| 2011/0176106 A1 | 7/2011 | Lewkowski |
| 2014/0192213 A1* | 7/2014 | Han ....................... H04N 21/00 348/218.1 |
| 2016/0165220 A1 | 6/2016 | Fujimaki et al. |
| 2018/0368763 A1 | 12/2018 | Seo |

(Continued)

FOREIGN PATENT DOCUMENTS

| JP | 09285468 A * | 11/1997 |
| JP | 11-225968 A  | 8/1999 |

(Continued)

OTHER PUBLICATIONS

Extended European Search Report issued Sep. 29, 2022, in corresponding European Patent Application No. 22171882.8, 7 pages.

(Continued)

*Primary Examiner* — Michael Lee
(74) *Attorney, Agent, or Firm* — Oblon, McClelland, Maier & Neustadt, L.L.P.

(57) ABSTRACT

An imaging device that includes a housing mounted on the head of a subject, a first camera that is held by the housing and captures an image of one eyeball of the subject, a second camera that is held by the housing and captures an image of the other eyeball of the subject, controller circuitry that synchronizes together the first image captured by the first camera and the second image captured by the second camera, and communication circuitry that externally transmits the synchronized first and second images.

15 Claims, 15 Drawing Sheets

(56) References Cited

U.S. PATENT DOCUMENTS

| | | | |
|---|---|---|---|
| 2020/0154025 A1 | 5/2020 | Wakatsuki | |
| 2020/0253532 A1* | 8/2020 | Jumaa | A61B 3/14 |
| 2022/0071484 A1 | 3/2022 | Seo | |
| 2022/0151489 A1* | 5/2022 | Khan | A61B 3/0008 |
| 2022/0354414 A1* | 11/2022 | Funabiki | A61B 3/005 |

FOREIGN PATENT DOCUMENTS

| | | |
|---|---|---|
| JP | 2001-321342 A | 11/2001 |
| JP | 2014-104120 A | 6/2014 |
| JP | 2016-33611 A | 3/2016 |
| JP | 2018-207453 A | 12/2018 |
| JP | 6638325 B2 | 1/2020 |
| WO | WO 2006/047816 A1 | 5/2006 |
| WO | WO 2017/044130 A1 | 3/2017 |
| WO | WO 2020/116669 A1 | 6/2020 |

OTHER PUBLICATIONS

Japanese Office Action issued May 30, 2023 in Japanese Application 2021-079598, (with unedited computer-generated English translation), 7 pages.

\* cited by examiner

IMAGING DEVICE, OCULAR MOVEMENT DATA PROCESSING SYSTEM, AND CONTROL METHOD

BACKGROUND

Field

The present disclosure relates to an imaging device, an ocular movement data processing system, and a control method.

Description Of The Background Art

Conventionally, in making a diagnosis of vertigo, disequilibrium and the like in departments of otorhinolaryngology, neurology, neurosurgery, and the like, equilibrium examinations have been widely carried out to examine how an eyeball moves in response to stimulation of an eye, a head, or an ear. Japanese Patent Laying-Open No. 2014-104120 discloses, as a method used in an equilibrium examination for recording and observing an ocular movement, a method in which an eyeball is imaged by an imaging device and a video thereof is observed and recorded to obtain objective ocular movement image data.

SUMMARY

The ocular movement examination apparatus disclosed in Japanese Patent Laying-Open No. 2014-104120 images movement of an eyeball of a subject with an imaging camera. However, when the subject's head position is changed while ocular movement is imaged, the subject may for example close one eye on the inclined side. When this one eye's ocular movement is alone imaged with the imaging camera, appropriate diagnosis cannot be performed based on image data of the ocular movement. In addition, when examining a subject with a symptom of vertigo, it is often difficult not only for elderly subjects but also other subjects to keep both eyes open, and image data of ocular movement allowing appropriate diagnosis may not be obtained.

The present disclosure has been made in order to solve such a problem, and an object of the present disclosure is to provide an imaging device, an ocular movement data processing system, and a control method capable of obtaining image data of ocular movement allowing appropriate diagnosis.

According to the present disclosure, there is provided an imaging device that images an eyeball in an equilibrium examination. The imaging device comprises a housing that is mounted on the head of a subject, a first imaging unit that is held by the housing and captures an image of one eyeball of the subject, a second imaging unit that is held by the housing and captures an image of the other eyeball of the subject, a control unit that synchronizes together a first image captured by the first imaging unit and a second image captured by the second imaging unit, and a communication unit that externally transmits the first and second images synchronized by the control unit.

According to the present disclosure, there is provided an ocular movement data processing system that processes ocular movement data in an equilibrium examination. The ocular movement data processing system comprises an imaging device that captures an image of an eyeball of a subject, and a data processing device that receives data from the imaging device and processes the data, the imaging device including a housing that is mounted on the head of a subject, a first imaging unit that is held by the housing and captures an image of one eyeball of the subject, a second imaging unit that is held by the housing and captures an image of the other eyeball of the subject, a control unit that synchronizes together a first image captured by the first imaging unit and a second image captured by the second imaging unit, and a communication unit that externally transmits the first and second images synchronized by the control unit, the data processing device including a receiving unit that receives the synchronized first and second images from the imaging device, and a processing unit that subjects the received, synchronized first and second images to prescribed data processing.

According to the present disclosure, there is provided a method for control by an imaging device that includes a housing that is mounted on the head of a subject, a first imaging unit that is held by the housing and captures an image of one eyeball of the subject, a second imaging unit that is held by the housing and captures an image of the other eyeball of the subject, to capture an image of the eyeballs in an equilibrium examination. The control method comprises the steps of: causing the first imaging unit and the second imaging unit to capture an image of the eyeballs of the subject; synchronizing together a first image captured by the first imaging unit and a second image captured by the second imaging unit; and externally transmitting the synchronized first and second images.

The foregoing and other objects, features, aspects and advantages of the present disclosure will become more apparent from the following detailed description of the present disclosure when taken in conjunction with the accompanying drawings.

DETAILED DESCRIPTION OF THE EMBODIMENTS

Figure 1:
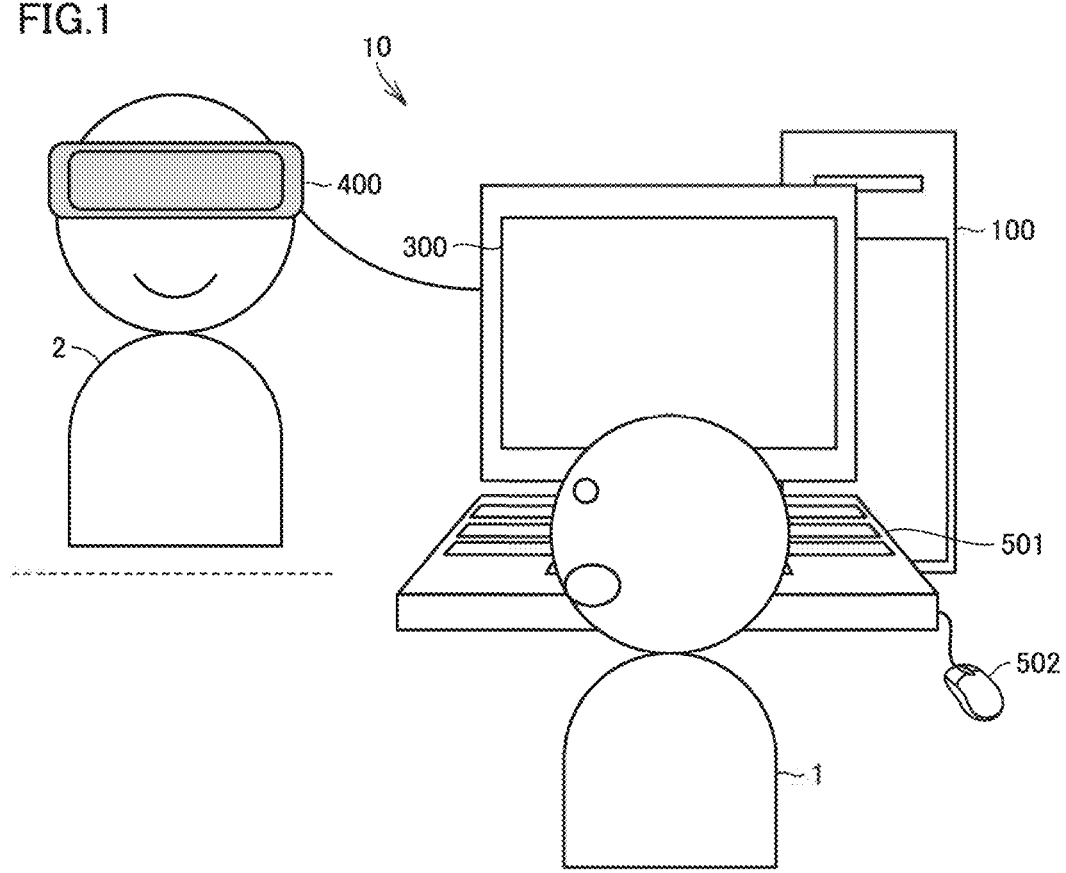
FIG. 1 is a schematic diagram showing a configuration of an ocular movement data processing system according to a first embodiment.

Embodiments of the present disclosure will be described in detail with reference to the drawings. In the drawings, identical or equivalent components are identically denoted and will not be described redundantly.

First Embodiment

Figure 2A:
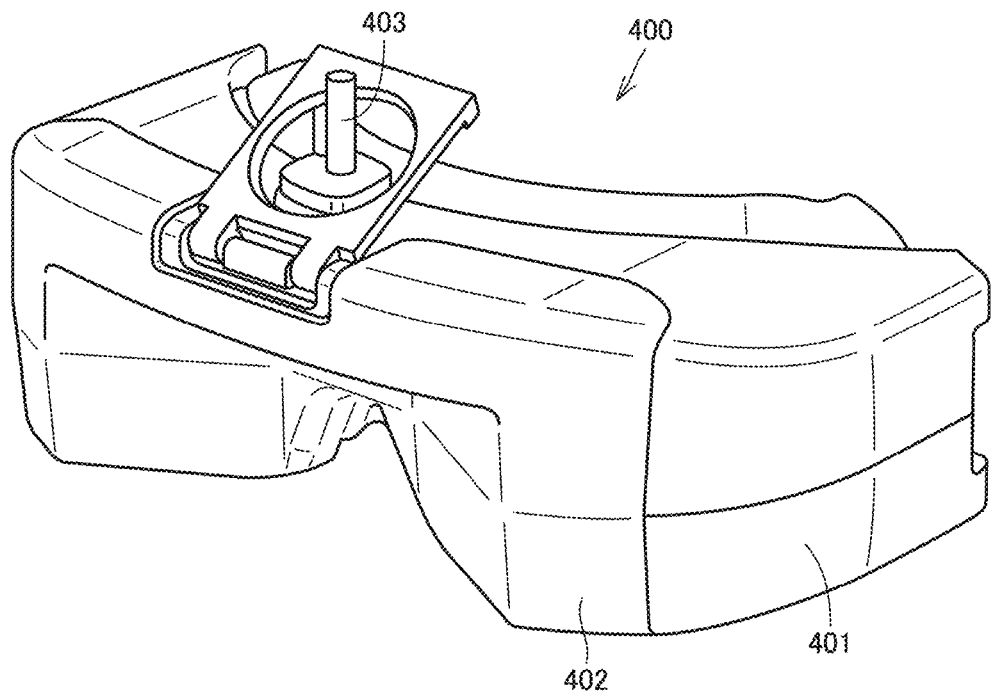
FIG. 2A is a schematic diagram for illustrating a configuration of an imaging device according to the first embodiment.
Figure 2B:
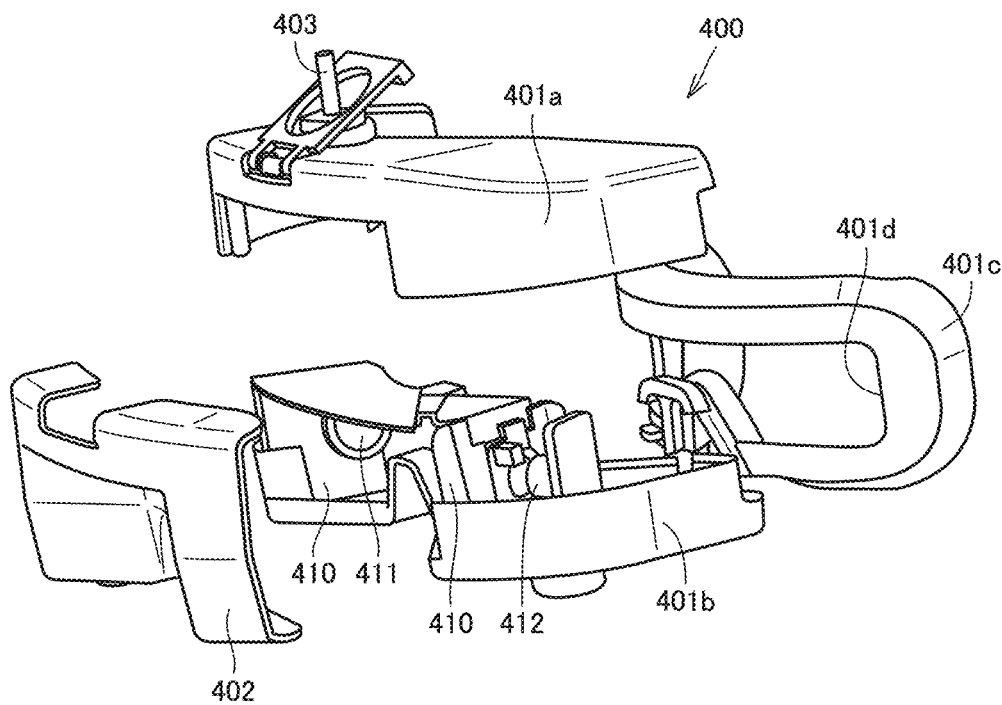
FIG. 2B is a schematic diagram for illustrating the configuration of the imaging device according to the first embodiment.
Figure 3:
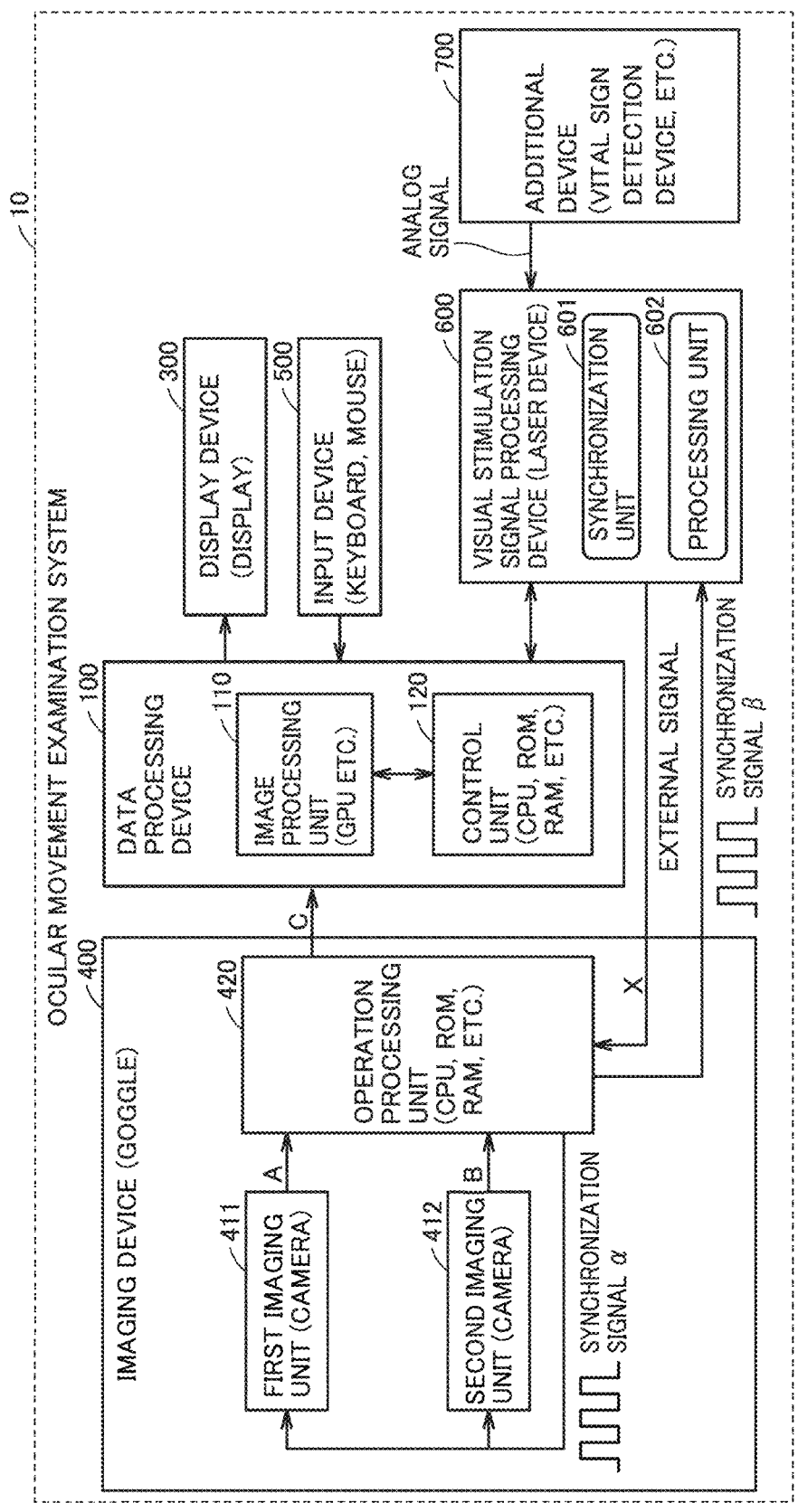
FIG. 3 is a block diagram generally showing a configuration of the ocular movement data processing system according to the first embodiment.

An ocular movement data processing system and an imaging device according to a first embodiment will be described with reference to the drawings. FIG. 1 is a schematic diagram showing a configuration of an ocular movement data processing system 10 according to the first embodiment. FIGS. 2A and 2B are schematic diagrams for illustrating a configuration of an imaging device 400 according to the embodiment. FIG. 3 is a block diagram generally showing a configuration of ocular movement data processing system 10 according to the first embodiment.

An operator 1 can diagnose vertigo of a subject 2 with ocular movement data processing system 10. Note that an "operator" may be any person who uses ocular movement data processing system 10, such as doctors belonging to clinics, general hospitals, university hospitals and the like; teachers, student and the like of medical colleges; and the like. It should be noted that the operator may belong not only to medical departments of ophthalmology, otorhinolaryngology or the like specialized for treatment of vertigo, but also other medical departments such as internal medicine and dentistry. A "subject" may be any person to be diagnosed through ocular movement data processing system 10, such as a patient of a clinic, a general hospital or a university hospital, or a subject in a medical college. "Vertigo" includes a state of subject 2 who suffers some abnormality in his/her vision, such as rotary vertigo causing a vision to spin around, floating dizziness causing a floating sensation, and syncopic dizziness causing a vision to black out.

As shown in FIG. 1, ocular movement data processing system 10 according to the first embodiment comprises a data processing device 100. A display 300, an imaging device 400, a keyboard 501, and a mouse 502 are connected to data processing device 100. Display 300 is an example of a display device. Keyboard 501 and mouse 502 are an example of an input device.

In general, vertigo is diagnosed through observation of nystagmus (an involuntary movement of a rhythmically moving eyeball). Nystagmus includes spontaneous nystagmus that occurs spontaneously with no stimulation applied, and evoked nystagmus caused when stimulation is applied. Further, evoked nystagmus includes positional nystagmus evoked when a head position is displaced, and a positioning nystagmus evoked when a body position is displaced. For evoked nystagmus, it is known that when a physiological rotational stimulus or the like is applied to the head, in particular, the eyeballs move opposite to the head in order to stabilize the field of view, and such a phenomenon is also referred to as vestibulo ocular reflex (VOR).

Specifically, in ocular movement data processing system 10, in order to observe subject 2 for nystagmus, imaging device 400 images the eyeballs of subject 2, and data processing device 100 processes, stores, and displays the image data. Accordingly, data processing device 100 is connected to imaging device 400. Imaging device 400 is a goggle-shaped device mounted on the head of subject 2, and captures an image of the eyeballs of subject 2 and obtains image data of an ocular movement for use in diagnosis of vertigo. As shown in FIG. 1, while subject 2 has imaging device 400 mounted on his/her head, operator 1 performs a nystagmus examination and thus obtains image data of ocular movement of subject 2, and inputs the obtained image data to data processing device 100. Data processing device 100 processes the image data obtained by imaging device 400 and provides operator 1 with information necessary for diagnosis of vertigo.

Imaging device 400 shown in FIG. 2A is in a state such that it has a front side with a shading cover 402 attached thereto. A wiring 403 is provided on an upper surface of housing 401 for connection to data processing device 100. Note that imaging device 400 may be connected to data processing device 100 not only via a wire but also wirelessly insofar as a sufficient transmission rate is ensured for transmission of image data.

Imaging device 400 shown in FIG. 2B is shown disassembled into an upper housing 401a, a lower housing 401b, and an eyepiece 401c brought into contact with subject 2. Lower housing 401b is provided with a first imaging unit 411 that is an infrared imaging device that captures an image of the right eye of subject 2, and a second imaging unit 412 that is an infrared imaging device that captures an image of the left eye of subject 2. Although not shown, upper housing 401a is provided with an operation processing unit 420 shown in FIG. 3.

Eyepiece 401c has an opening 401d such that first and second imaging units 411 and 412 can image the eyeballs of subject 2 while subject 2 is covered in front of his/her eyes. Eyepiece 401c is formed of synthetic resin or soft rubber having appropriate flexibility and elasticity so as to be in close contact with the face of subject 2 when the imaging device is mounted on the head of subject 2.

Shading cover 402 is provided with a magnet, for example, and easily detachably attachable to imaging device 400. When shading cover 402 is detached from imaging device 400, subject 2 can see ahead through a hot mirror 410 and thus see an index or the like emitted from a visual stimulation signal processing device 600. Hot mirror 410 is an optical component that is a glass or resin plate coated with a material which transmits visible light and reflects infrared light to obtain an infrared image of an eyeball of the subject while ensuring a field of view for the subject. First and second imaging units 411 and 412 capture an image of the eyeballs of subject 2 reflected by hot mirror 410.

In imaging device 400, as shown in FIG. 3, image data A from first imaging unit 411 and image data B from second imaging unit 412 are processed by operation processing unit 420 and transmitted to data processing device 100 as image data C. First imaging unit 411 includes an infrared imaging device, and a processing circuit (not shown) that attaches information of a frame number and a time stamp (first information) to an image that is captured by the infrared imaging device for each frame to provide image data A and output image data A to operation processing unit 420. The information included in the first information is not limited to a frame number and a time stamp, and may be information of at least one of the frame number and the time stamp, and may include information such as a frame rate, an amount of exposure, and a contrast. Similarly, second imaging unit 412 includes an infrared imaging device, and a processing circuit (not shown) that attaches information of a frame number and a time stamp (second information) to an image that is captured by the infrared imaging device for each frame to provide image data B and output image data B to operation processing unit 420. The information included in the second information is not limited to a frame number and a time stamp, and may be information of at least one of the frame number and the time stamp, and may include information such as a frame rate, an amount of exposure, and a contrast.

First and second imaging units 411 and 412 can capture an image at 60 frames/sec or 240 frames/sec. The infrared imaging device used for first and second imaging units 411 and 412 is, for example, a CMOS (Complementary Metal Oxide Semiconductor) sensor, a CCD (Charge Coupled Device), or the like capable of capturing an infrared ray.

Operation processing unit 420 performs operation-processing, that is, generates image data C by synchronizing together an image captured by first imaging unit 411 (a first image) and an image captured by second imaging unit 412 (a second image). Accordingly, operation processing unit 420 is a computing entity that performs processing of image data, and it is an example of a computer and for example is composed of a central processing unit (CPU), a field-programmable gate array (FPGA), or the like. Furthermore, operation processing unit 420 includes memories such as a random access memory (RAM) for storing images and the like and a read only memory (ROM) for storing programs and the like. In addition to the configuration in which operation processing unit 420 is executed as a control unit (a controller) that synchronizes together the image captured by first imaging unit 411 and the image captured by second imaging unit 412, operation processing unit 420 also has a configuration in which operation processing unit 420 is executed as a communication unit (a communication circuit) that externally transmits the synchronized images.

Operation processing unit 420 may use a synchronization signal as a method for synchronizing together the image captured by first imaging unit 411 and the image captured by second imaging unit 412. Specifically, operation processing unit 420 transmits a synchronization signal α to each of first and second imaging units 411 and 412. First and second imaging units 411 and 412 can use synchronization signal α as a start signal to start an operation (exposure→obtaining a signal→transmission) to obtain their respectively captured first and second images in synchronization. When first and second imaging units 411 and 412 are configured to have no memory for storing two or more pieces of image data, and one imaging unit fails to obtain a signal, operation processing unit 420 can only obtain one piece of image data, and will thus never obtain unsynchronized image data.

When first and second imaging units 411 and 412 have a configuration to each provide an image with a time stamp, then, there is a method for synchronization based on the time stamp added to each image. The time stamp is generated based on time counted by each of counters of first and second imaging units 411 and 412, and in order to use it for synchronization of images, it is necessary to synchronize the time of the counter of first imaging unit 411 and the time of the counter of second imaging unit 412 together. Accordingly, operation processing unit 420 transmits a synchronization signal α to each of first and second imaging units 411 and 412, and, based on synchronization signal α, first and second imaging units 411 and 412 synchronize and thus adjust the time counted by each counter and add a time stamp to their respective images. Based on each time stamp adjusted by synchronization signal α, operation processing unit 420 can reliably synchronize the image captured by first imaging unit 411 and the image captured by second imaging unit 412 together to obtain a right eye image and a left eye image of the same timing. In particular, when first and second imaging units 411 and 412 capture images at 240 frames/sec, simply correlating the images output from the respective imaging units with each other does not provide a right eye image and a left eye image of the same timing and appropriate diagnosis cannot be performed.

Synchronization signal α transmitted by operation processing unit 420 to each of first and second imaging units 411 and 412 is a clock signal repeated periodically as prescribed (for example at 60 Hz). This is not exclusive, however, and operation processing unit 420 may transmit a single-shot pulse signal as synchronization signal α to each of first and second imaging units 411 and 412, as timed when started, as prescribed, or the like.

Further, operation processing unit 420 may not transmit synchronization signal a to each of first and second imaging units 411 and 412, and may instead synchronize the time counted by each counter, for example as timed when first and second imaging units 411 and 412 are powered on. Further, operation processing unit 420 may not provide synchronization based on the time stamp added to each image; rather, when first and second imaging units 411 and 412 each have a configuration to add a frame number to an image, operation processing unit 420 may provide synchronization based on the frame number added to each image.

Figure 4:
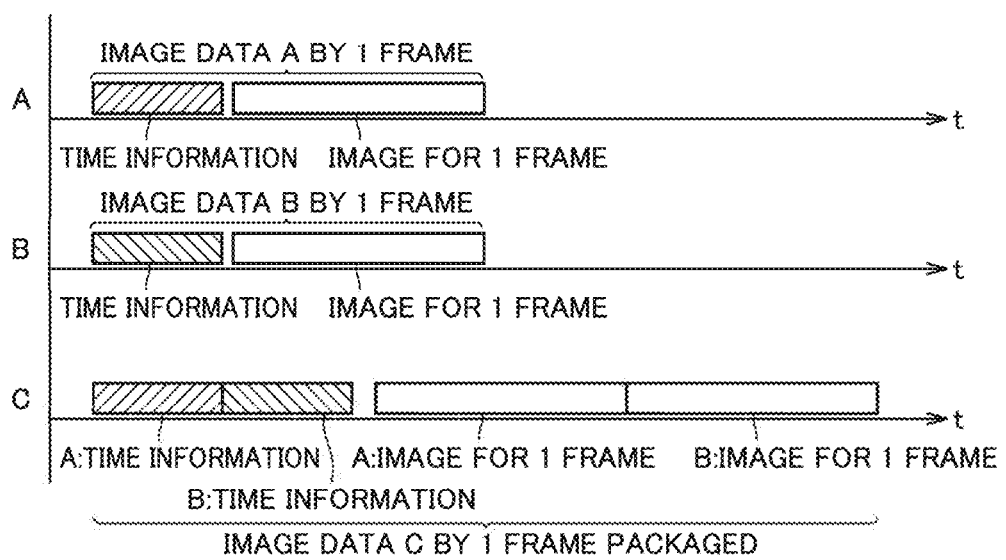
FIG. 4 is a schematic diagram representing image data of a first imaging unit and that of a second imaging unit, and image data output by an operation processing unit.

FIG. 4 is a schematic diagram representing image data of each of first and second imaging units 411 and 412 and image data output by operation processing unit 420. As shown in FIG. 4, first imaging unit 411 adds time information (a frame number, a time stamp, etc.) to an image of one frame and outputs the image with the time information as image data A. Similarly, as shown in FIG. 4, second imaging unit 412 adds time information (a frame number, a time stamp, etc.) to an image of one frame and outputs the image with the time information as image data B. As shown in FIG. 4, operation processing unit 420 processes the image of one frame of first imaging unit 411 and the image of one frame of second imaging unit 412 including the same time information as one image, and outputs the processed image and the time information of first imaging unit 411 and that of second imaging unit 412 as one image data C. Image data C provides both eyes' real-time images as one image data, and is thus suitable for simultaneously displaying both eyes' images in data processing device 100 without delay.

Figure 5:
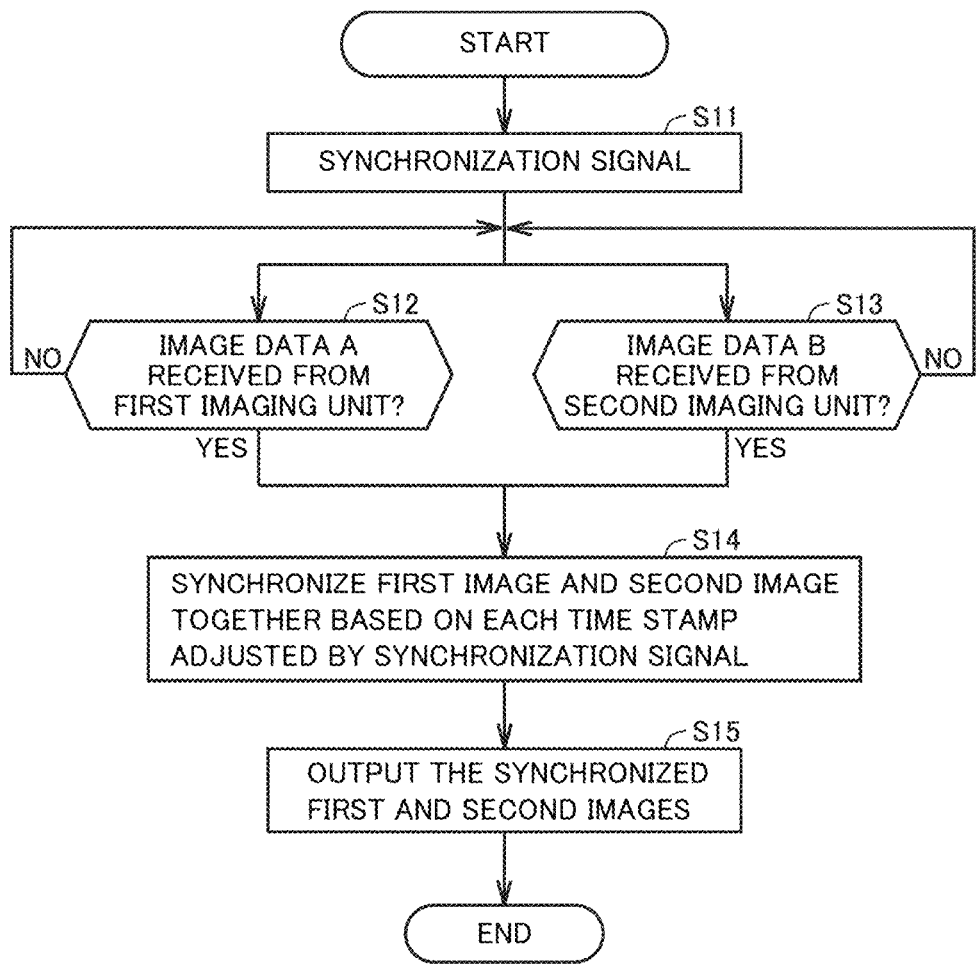
FIG. 5 is a flowchart of a method for controlling the imaging device according to the first embodiment.

Hereinafter reference will be made to a flowchart to describe a control method in which imaging device 400 synchronizes an image captured by first imaging unit 411 and an image captured by second imaging unit 412 together to output an image. FIG. 5 is a flowchart of a method for controlling imaging device 400 according to the first embodiment. Initially, operation processing unit 420 transmits synchronization signal α to first and second imaging units 411 and 412 (step S11). First and second imaging units 411 and 412 perform adjustment based on synchronization signal α to synchronize the time counted by each counter.

Operation processing unit 420 determines whether image data A (first image data) is received from first imaging unit 411 (step S12). When image data A is not received (NO in step S12), operation processing unit 420 returns to step S12. When image data A is received (YES in step S12), operation processing unit 420 determines whether image data B (second image data) is received from second imaging unit 412 (step S13). When image data B is not received (NO in step S13), operation processing unit 420 returns to step S13. As shown in the flowchart of FIG. 5, operation processing unit 420 processes image data A received from first imaging unit 411 and image data B received from second imaging unit 412 at the same time.

When image data B is received (YES in step S13), operation processing unit 420 synchronizes the image captured by first imaging unit 411 (a first image) and the image captured by second imaging unit 412 (a second image) together based on each time stamp adjusted by synchronization signal α (step S14). When in step S12 and step S13 information of either one of image data A from the first imaging unit and image data B from the second imaging unit is not received and another information is received, the received one of information of image data A and B may alone be synchronized with the received other information. When either one of information is not received, then the synchronization step of step 14 may not be performed and the control may return to step S12 and step S13. Operation processing unit 420 outputs the image captured by first imaging unit 411 (the first image) and the image captured by second imaging unit 412 (the second image) that are synchronized together (step S15). That is, as shown in FIG. 4, image data A and image data B captured at the same time are synthesized, based on the time stamp, to be adjacent to each other to generate and output image data C.

Figure 6:
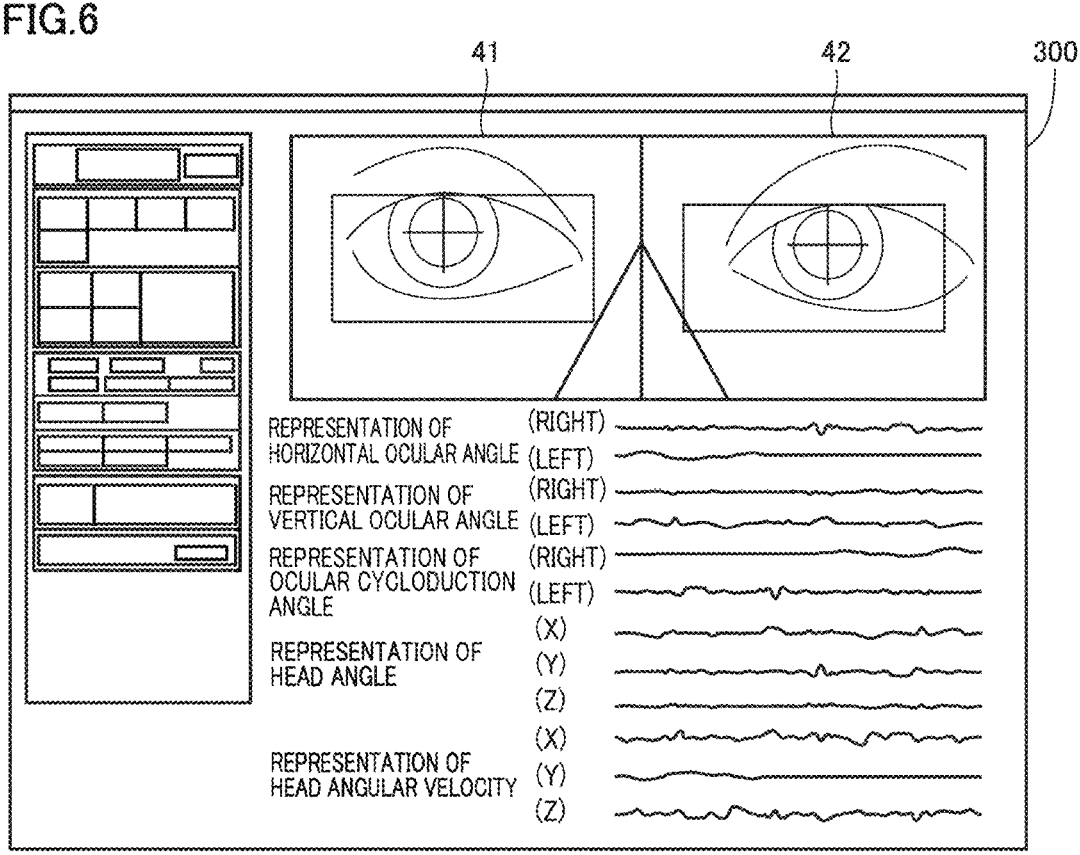
FIG. 6 is a schematic diagram showing an example of an image of the eyeballs of a subject and data of an ocular movement thereof displayed on a display of the data processing device.

Subsequently, the image captured by first imaging unit 411 (the first image) and the image captured by second imaging unit 412 (the second image) that are synchronized together are transmitted to data processing device 100, and processing of ocular movement data required for diagnosis of vertigo is performed. FIG. 6 is a schematic diagram showing an example of an image of the eyeballs of subject 2 and data of an ocular movement thereof displayed on display 300 of data processing device 100. The example of displaying by display 300 shown in FIG. 6 displays on a screen at an upper side a first image 41 captured by first imaging unit 411 and a second image 42 captured by second imaging unit 412. Data processing device 100 can sample first image 41 and second image 42 for each frame, binarize the sampled images to perform elliptical approximation, or apply a template image to the sampled images to perform pattern-matching to detect each eyeball's pupil contour and center. An image indicating each eyeball's pupil contour and center, as detected by data processing device 100, is superimposed and displayed on first image 41 and second image 42 displayed on display 300.

As shown in FIG. 3, data processing device 100 includes an image processing unit 110 and a control unit 120. Image processing unit 110 is composed of a graphics processing unit (GPU) or the like, and can cause display 300 to display first image 41 and second image 42, and superimpose an image indicating each eyeball's pupil contour and center on first image 41 and second image 42 and thus display the superimposed images on display 300. Control unit 120 is a computing entity which performs elliptical approximation or uses a template image to perform pattern-matching or the like to detect an eyeball's pupil contour and center. It is an example of a computer composed for example of a CPU, an FPGA, or the like. Further, control unit 120 includes memory such as a RAM used to store an image or the like and a ROM having a program or the like stored therein. In addition to the configuration in which control unit 120 is executed as a processing unit (a processor) that subjects the synchronized first and second images 41 and 42 to prescribed data processing, control unit 120 also has a configuration in which control unit 120 is executed as a receiving unit (a receiving circuit) that receives the synchronized first and second images 41 and 42 from imaging device 400.

Control unit 120 further determines a horizontal ocular angle (right), a vertical ocular angle (right) and an ocular cycloduction angle (right) from first image 41, and a horizontal ocular angle (left), a vertical ocular angle (left) and an ocular cycloduction angle (left) from second image 42, each through an operation. Specifically, control unit 120 determines each eyeball's pupil contour and center position of first image 41 and second image 42 as detected for each frame, and from the position calculates horizontal ocular angles (right and left), vertical ocular angles (right and left), and ocular cycloduction angles (right and left). Data processing device 100 records how the horizontal ocular angles (right and left), vertical ocular angles (right and left), and ocular cycloduction angles (right and left) calculated by control unit 120 change in value with time, and causes display 300 to display it on a screen at a lower side.

Although not shown, imaging device 400 is provided with a head sensor including an acceleration sensor and an angular velocity sensor, and the head sensor outputs a measurement signal corresponding to the movement of the head of subject 2. The head sensor may be mounted on the head of subject 2 separately from imaging device 400. Operation processing unit 420 or control unit 120 determines a head angle and a head angular velocity through an operation based on the measurement signal received from the head sensor. Data processing device 100 records how the head angle and head angular velocity calculated by operation processing unit 420 or control unit 120 change in value with time, and causes display 300 to display it on the screen at a lower side. Head angle and head angular velocity are represented in a graph, which represent them in value along each of three axes (X-, Y- and Z-axes).

Figure 7:
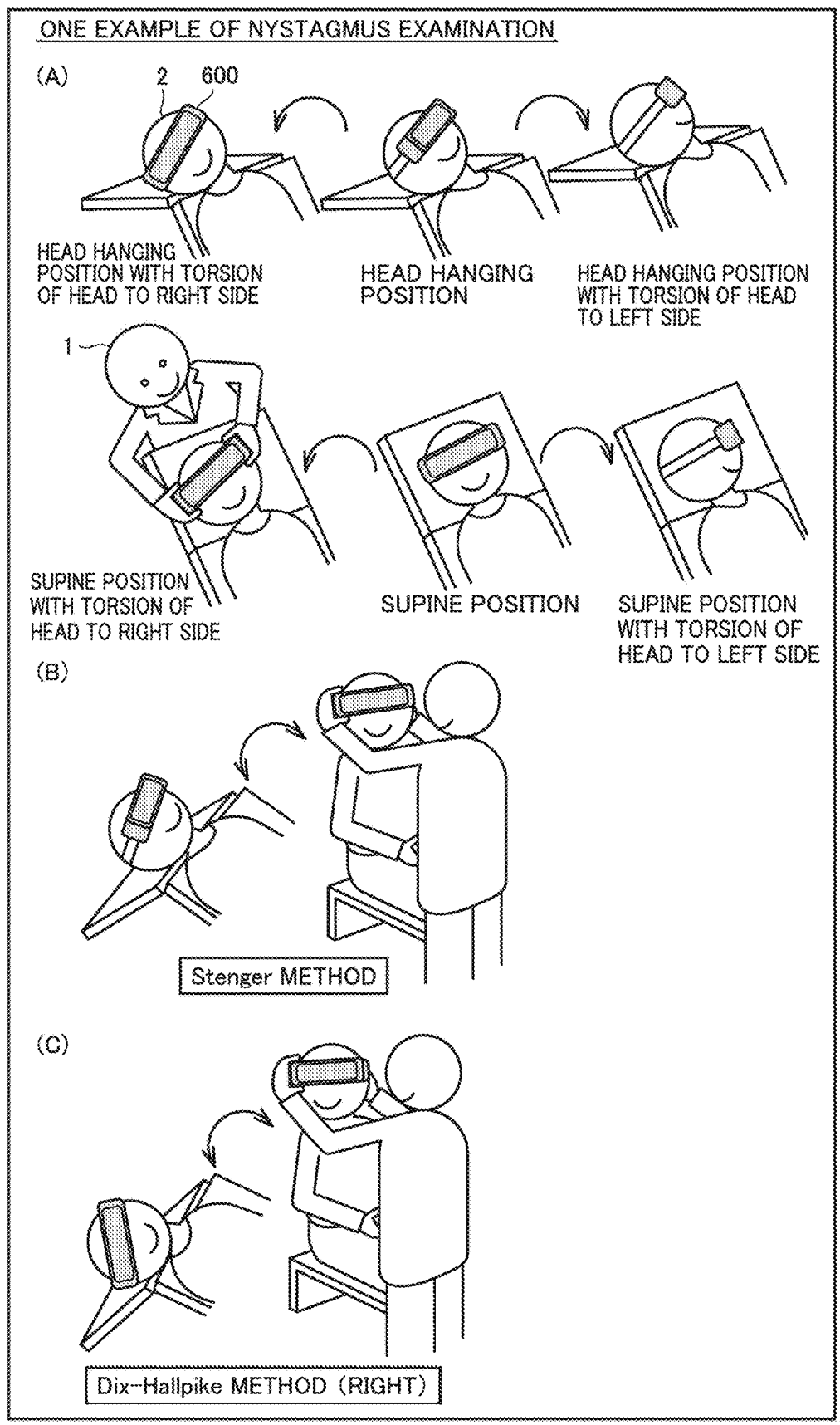
FIG. 7 is a schematic diagram for illustrating an example of a nystagmus examination.

Further, an example of a nystagmus examination used in diagnosis of vertigo will be described. FIG. 7 is a schematic diagram for illustrating an example of a nystagmus examination. The nystagmus examination is performed under a prescribed condition. For example, in an examination for spontaneous nystagmus, operator 1 diagnoses vertigo based on an ocular movement of subject 2 while the subject has his/her head fixed and thus gazes frontward. In an examination for positional nystagmus, as shown in FIG. 7A, operator 1 diagnoses vertigo based on an ocular movement of subject 2 induced as the subject displaces his/her head's position to various positions. In an examination for positioning nystagmus, as shown in FIGS. 7(B) and 7(c), operator 1 diagnoses vertigo based on an ocular movement of subject 2 induced as the operator 1 displaces the subject's bodily and head positions.

Figure 8:
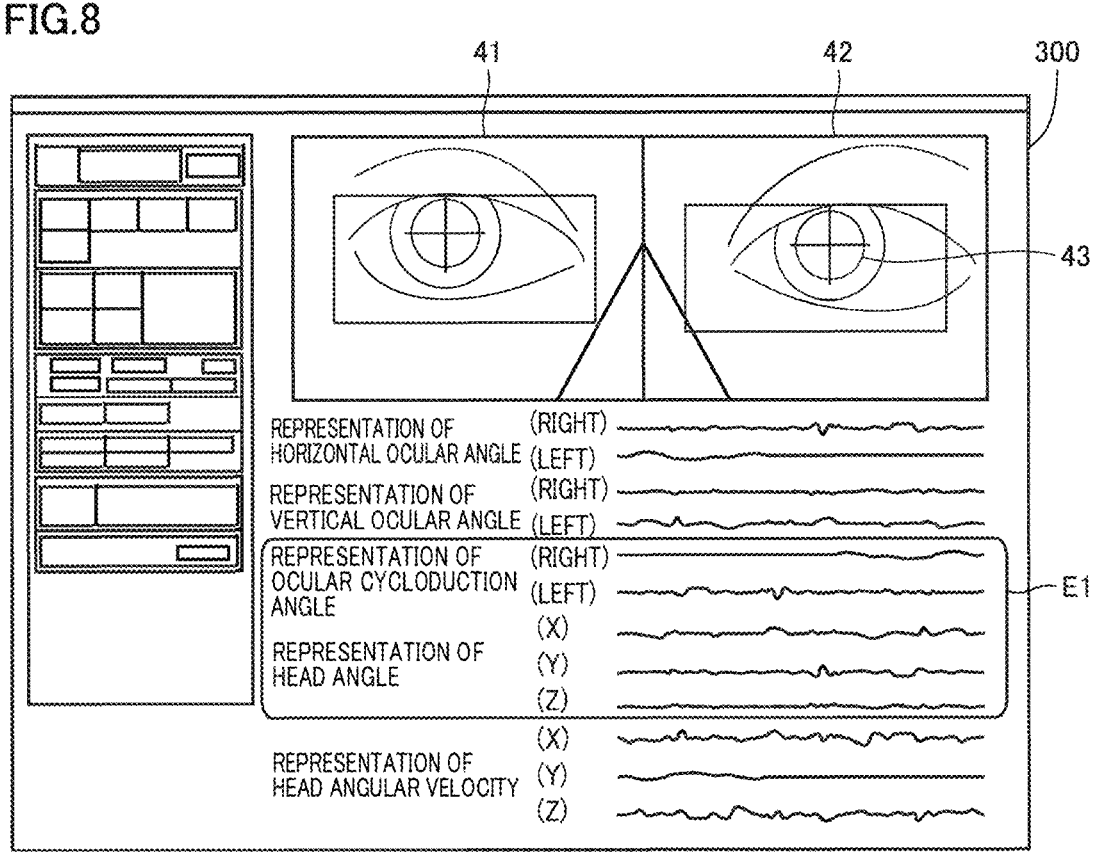
FIG. 8 is a schematic diagram showing an example of an image of the eyeballs of a subject and data of an ocular movement thereof displayed on a display in a nystagmus examination.

FIG. 8 is a schematic diagram showing an example of an image of the eyeballs of subject 2 and data of an ocular movement thereof displayed on a display in a nystagmus examination. Data processing device 100 in the nystagmus examination processes ocular movement data from an image of the pupil, iris pattern and the like of an eyeball of subject 2. When subject 2 has only a single eye imaged with an imaging device during a nystagmus examination, and the subject assumes some head position, the subject may lower one eyelid or the like, and the imaging device may be unable to constantly obtain an image of the eyeball. In contrast, imaging device 400 obtains images of both eyes of subject 2 through first and second imaging units 411 and 412, respectively, and synchronizes the images and thus processes data, and even if the subject lowers one eyelid or the like and one eyeball's image cannot be obtained, the other eyeball's image of the same timing has been obtained without fail. Thus, even when subject 2 changes his/her head position during a nystagmus examination, data processing device 100 ensures that an image of an eyeball allowing data to be processed is obtained, and data processing device 100 can thus steadily process ocular movement data of subject 2. In the example shown in FIG. 8, the nystagmus examination is performed by processing data E1 of how ocular cycloduction angles (right and left) and a head angle change with time.

Figure 9:
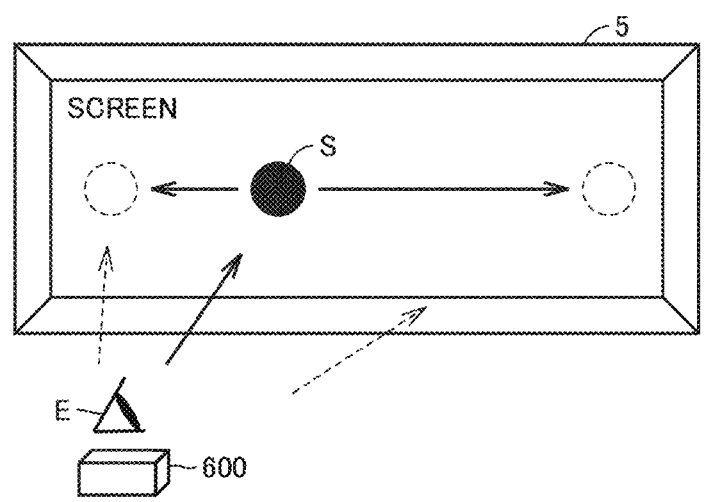
FIG. 9 is a schematic diagram for illustrating an example of a visual stimulation test.

Hereinafter, an example of a visual stimulation test employed in diagnosis of vertigo will be described. FIG. 9 is a schematic diagram for illustrating an example of a visual stimulation test. FIG. 9 shows a screen 5 for projecting a visual target S generated by visual stimulation signal processing device 600, and shows how visual target S is positionally moved rightward/leftward as it is positionally changed by visual stimulation signal processing device 600. Visual target S may positionally not be moved rightward/leftward and instead be moved upward/downward or upward/downward/rightward/leftward. When the visual stimulation test is performed, subject 2 wears imaging device 400 having detached therefrom shading cover 402 shown in FIG. 2A, and subject 2 can thus visually recognize visual target S projected on screen 5 through hot mirror 410.

Visual stimulation signal processing device 600 includes a laser device to generate a laser point on screen 5 shown in FIG. 9 and thus display the laser point as visual target S. As shown in FIG. 3, visual stimulation signal processing device 600 can transmit and receive data to and from data processing device 100, and also receives a synchronization signal β from imaging device 400. Visual stimulation signal processing device 600 includes a synchronization unit 601 and a processing unit 602. Based on synchronization signal β received from imaging device 400, synchronization unit 601 synchronizes and adjusts time counted by each counter and provides a time stamp to processing unit 602. Furthermore, visual stimulation signal processing device 600 is connectable to an additional device 700 such as a vital sign detection device. Visual stimulation signal processing device 600 receives an analog signal of a vital sign (a heart rate, a respiration rate, a blood pressure value, a pulse rate, etc.) from additional device 700, and converts the analog signal into a vital signal of a digital signal by processing unit 602. Visual stimulation signal processing device 600 includes the vital signal in an external signal of visual stimulation signal processing device 600, adds a time stamp of synchronization unit 601 to the external signal, and outputs the external signal with the time stamp to imaging device 400. The external signal output from visual stimulation signal processing device 600 includes information of the external device (visual stimulation signal processing device 600 and additional device 700), such as the vital signal of additional device 700 and a visual stimulation signal of visual stimulation signal processing device 600. In this case, time information added to image data C or time information added to image data A and B as shown in FIG. 4 is added to vital sign information. Note that the visual stimulation signal specifically includes a signal indicating that a visual target is projected on the screen and visual stimulation is thus generated, a positional signal (a signal of XY coordinates) of an index on the screen serving as visual stimulation, and the like.

Figure 10:
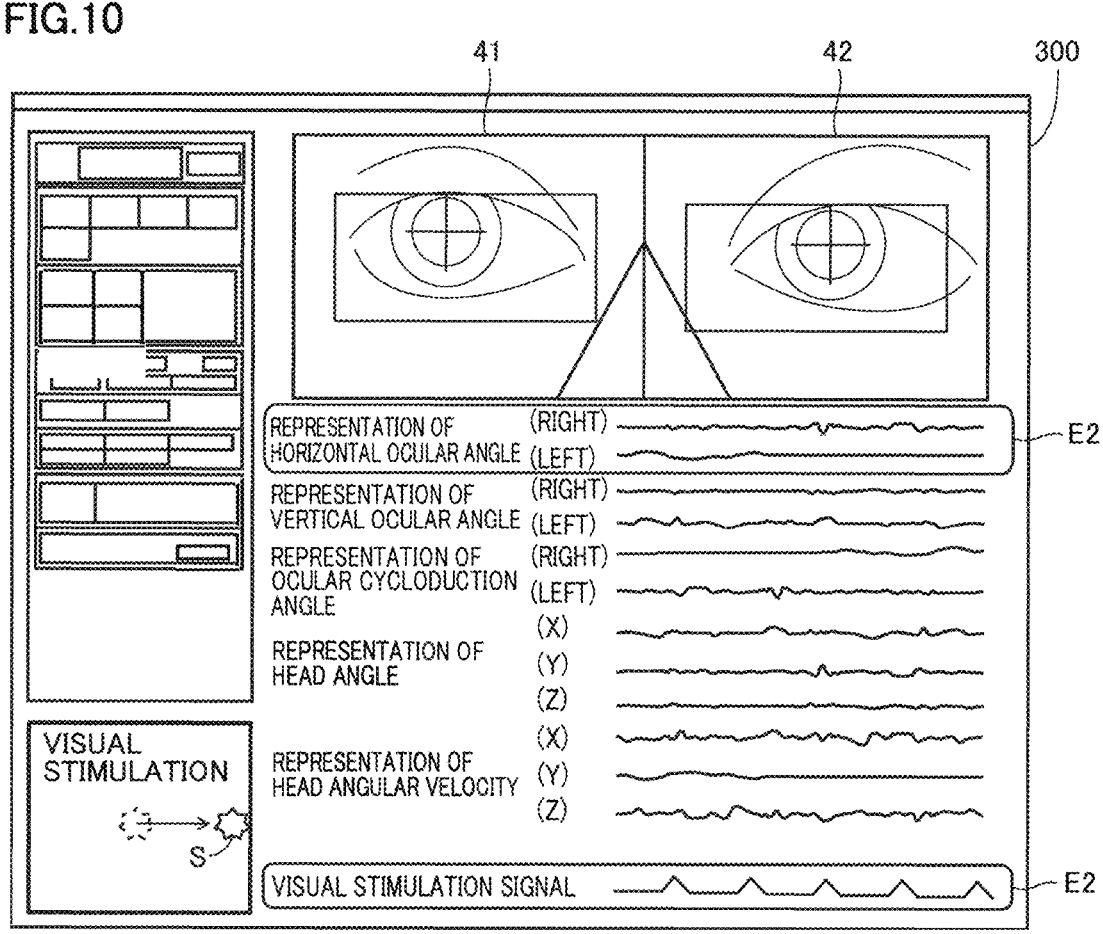
FIG. 10 is a schematic diagram showing an example of an image of the eyeballs of a subject and data of an ocular movement thereof displayed on a display in a visual stimulation test.

FIG. 10 is a schematic diagram showing an example of an image of the eyeballs of subject 2 and data of an ocular movement thereof displayed on a display in a visual stimulation test. Data processing device 100 in the FIG. 9 visual stimulation test processes ocular movement data from an image of the pupil, iris pattern and the like of an eyeball of subject 2. A pursuit eye movement test, which is an example of the visual stimulation test, examines how an eyeball of subject 2 follows visual target S. Accordingly, in the example shown in FIG. 10, data processing device 100 performs the pursuit eye movement test by processing data E2 of how horizontal ocular angles (right and left) and a horizontal visual stimulation angle change with time. Note that, in FIG. 10, display 300 displays on a screen at a lower side a graph corresponding to how a visual stimulation signal of those received from visual stimulation signal processing device 600 that indicates that visual stimulation is generated, changes with time. Further, display 300 displays on the screen at a lower left side that visual target S projected on screen 5 positionally moves from left to right, based on a signal of XY coordinates of visual target S included in the visual stimulation signal. When visual target S positionally moves upward/downward rather than rightward/leftward, data E2 needs to be how vertical ocular angles (right and left) and a vertical visual stimulation angle change with time, and when visual target S positionally moves upward/downward/rightward/leftward, data E2 needs to be how horizontal ocular angles (right and left), vertical ocular angles (right and left), a horizontal visual stimulation angle and a vertical visual stimulation angle change with time.

Another example of the visual stimulation test is a saccadic eye movement test. In the saccadic eye movement test, visual target S flashed on/off right and left alternately or the like is shown to subject 2 to test how the eyeballs of subject 2 move. Processing ocular movement data of subject 2 in the saccadic eye movement test requires sampling an image at a rate of 6 ms=166 fps or more. Accordingly, imaging device 400 is required to capture an image of the eyeballs of subject 2 at a high sampling rate of 240 fps rather than doing so at a normal sampling rate of 60 fps.

Figure 11:
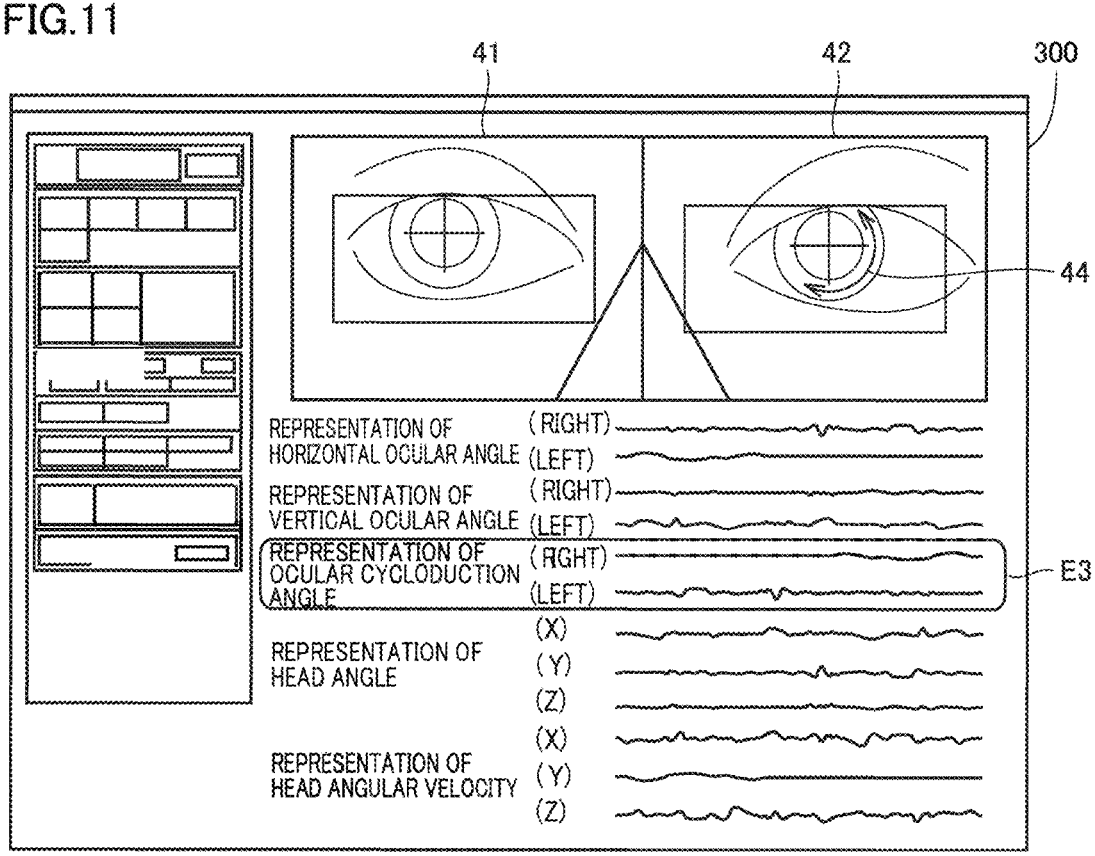
FIG. 11 is a schematic diagram showing an example of an image of the eyeballs of a subject and data of an ocular movement thereof displayed on a display when ocular cycloduction movement data is processed.

In addition, ocular cycloduction movement data may be processed in diagnosis of vertigo. FIG. 11 is a schematic diagram showing an example of an image of the eyeballs of subject 2 and data of an ocular movement thereof displayed on a display when ocular cycloduction movement data is processed. Data processing device 100 processes ocular cycloduction movement data from recognition (or pattern-matching) of an image of the pupil, iris pattern and the like of an eyeball of subject 2. When processing ocular cycloduction movement data, data processing device 100 detects ocular cycloduction movement, as indicated in FIG. 11 by an arrow 44, records how an ocular cycloduction angle changes with time, and causes display 300 to display it on a screen at a lower side. Data processing device 100 processes ocular cycloduction movement data of subject 2 by examining data E3 of how ocular cycloduction angles (right and left) change with time.

Figure 12:
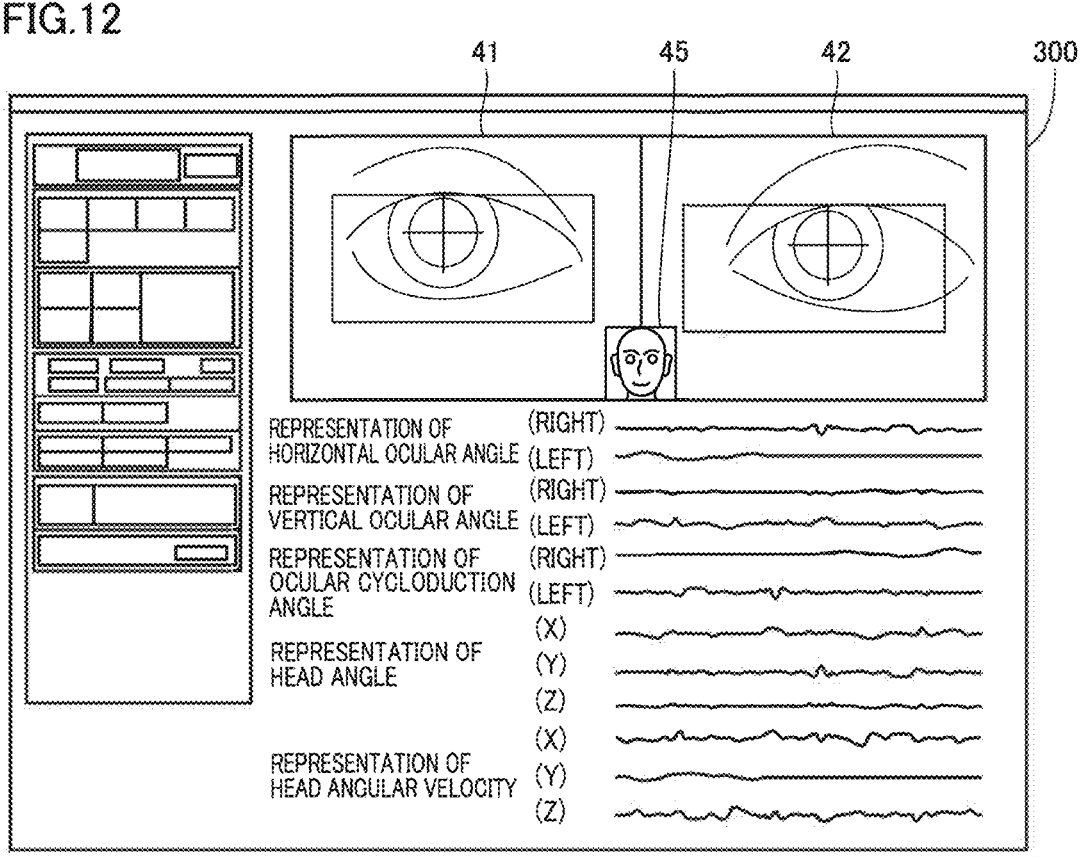
FIG. 12 is a schematic diagram of superimposing an image showing an orientation of the head of a subject on an image of the eyeballs of the subject, and causing a display to display the thus superimposed images.

Further, in diagnosis of vertigo, the orientation of the head is also important information along with ocular movement, and accordingly, operator 1 desires to be able to recognize an image of an eyeball and the orientation of the head simultaneously. Accordingly, data processing device 100 superimposes the image of the eyeball and an image representing the orientation of the head, one on the other, and causes display 300 to display the superimposed images. FIG. 12 is a schematic diagram of superimposing an image representing an orientation of the head of subject 2 on an image of the eyeballs of the subject, and causing a display to display the thus superimposed images. On the screen shown in FIG. 12 at an upper side are displayed first image 41 captured by first imaging unit 411 and second image 42 captured by second imaging unit 412, with an image 45 therebetween indicating the orientation of the head of subject 2. Image 45 indicating the orientation of the head of subject 2 shows in a 3D model of the head the orientation of the head based on information of a head angle and a head angular acceleration as measured by the head sensor. Image 45 indicating the orientation of the head of subject 2 is not limited to the 3D model of the head as shown in FIG. 12, and may for example be displayed in the form of a 2D model, textual information, etc.

As described above, imaging device 400 according to the first embodiment is a device that images an eyeball in an equilibrium examination. Imaging device 400 comprises housing 401 that is mounted on the head of subject 2, first imaging unit 411 that is held by housing 401 and captures an image of one eyeball of subject 2, second imaging unit 412 that is held by housing 401 and captures an image of the other eyeball of subject 2, operation processing unit 420 (a control unit) that synchronizes together first image 41 captured by first imaging unit 411 and second image 42 captured by second imaging unit 412, and operation processing unit 420 (a communication unit) that externally transmits the synchronized first and second images 41 and 42.

Thus, imaging device 400 according to the first embodiment synchronizes together first image 41 captured by first imaging unit 411 and second image 42 captured by second imaging unit 412, and can thus obtain image data of ocular movement allowing appropriately diagnosis.

The first imaging unit 411 adds first information to each captured first image 41 and outputs the image with the first information as image data A to operation processing unit 420 and second imaging unit 412 adds second information to each captured second image 42 and outputs the image with the second information as image data B to operation processing unit 420, and operation processing unit 420 synchronizes first image 41 and second image 42 together based on the first information included in image data A and the second information included in image data B and externally transmits the synchronized image data A and image data B. Thus, operation processing unit 420 can reliably synchronize first image 41 and second image 42 together based on the first information included in image data A and the second information included in image data B.

The operation processing unit 420 processes the synchronized first and second images 41 and 42 as one image, and operation processing unit 420 externally transmits image data C including the processed image and the corresponding first information and second information. Data processing device 100 receiving from operation processing unit 420 first image 41 and second image 42 processed as one image may simply cause display 300 to display the processed one image.

The operation processing unit 420 transmits synchronization signal α to first and second imaging units 411 and 412, and first and second imaging units 411 and 412 synchronize the first information and the second information together based on synchronization signal α. Operation processing unit 420 can thus reliably perform adjustment of synchronizing the first information of first imaging unit 411 and the second information of second imaging unit 412 together. The synchronization signal α transmitted to first and second imaging units 411 and 412 is a signal repeated periodically as prescribed.

The first information and the second information at least include information of a timestamp. Operation processing unit 420 can reliably synchronize first image 41 and second image 42 together based on a time stamp included in image data A and a time stamp included in image data B.

Ocular movement data processing system 10 according to the first embodiment is a system that processes ocular movement data in an equilibrium examination. Ocular movement data processing system 10 comprises imaging device 400 that captures an image of an eyeball of subject 2, and data processing device 100 that receives data from imaging device 400 and processes the received data. Imaging device 400 comprises housing 401 that is mounted on the head of subject 2, first imaging unit 411 that is held by housing 401 and captures an image of one eyeball of subject 2, second imaging unit 412 that is held by housing 401 and captures an image of the other eyeball of subject 2, operation processing unit 420 (a control unit) that synchronizes together first image 41 captured by first imaging unit 411 and second image 42 captured by second imaging unit 412, and operation processing unit 420 (a communication unit) that transmits the synchronized first and second images to data processing device 100. Data processing device 100 includes control unit 120 (a receiving unit) that receives the synchronized first and second images from imaging device 400, and control unit 120 (a processing unit) that subjects the received, synchronized first and second images to prescribed data processing.

A method of control by imaging device 400 according to the first embodiment comprises the steps of: causing first and second imaging units 411 and 412 to capture an image of the eyeballs of subject 2; synchronizing together first image 41 captured by first imaging unit 411 and second image 42 captured by second imaging unit 412; and externally transmitting the synchronized first and second images 41 and 42.

Second Embodiment

For ocular movement data processing system 10 according to the first embodiment is described a configuration in which first image 41 captured by first imaging unit 411 and second image 42 captured by second imaging unit 412 are synchronized together in imaging device 400. For an ocular movement data processing system according to a second embodiment will be described a configuration to further synchronize information of a sensor provided to imaging device 400.

Figure 13:
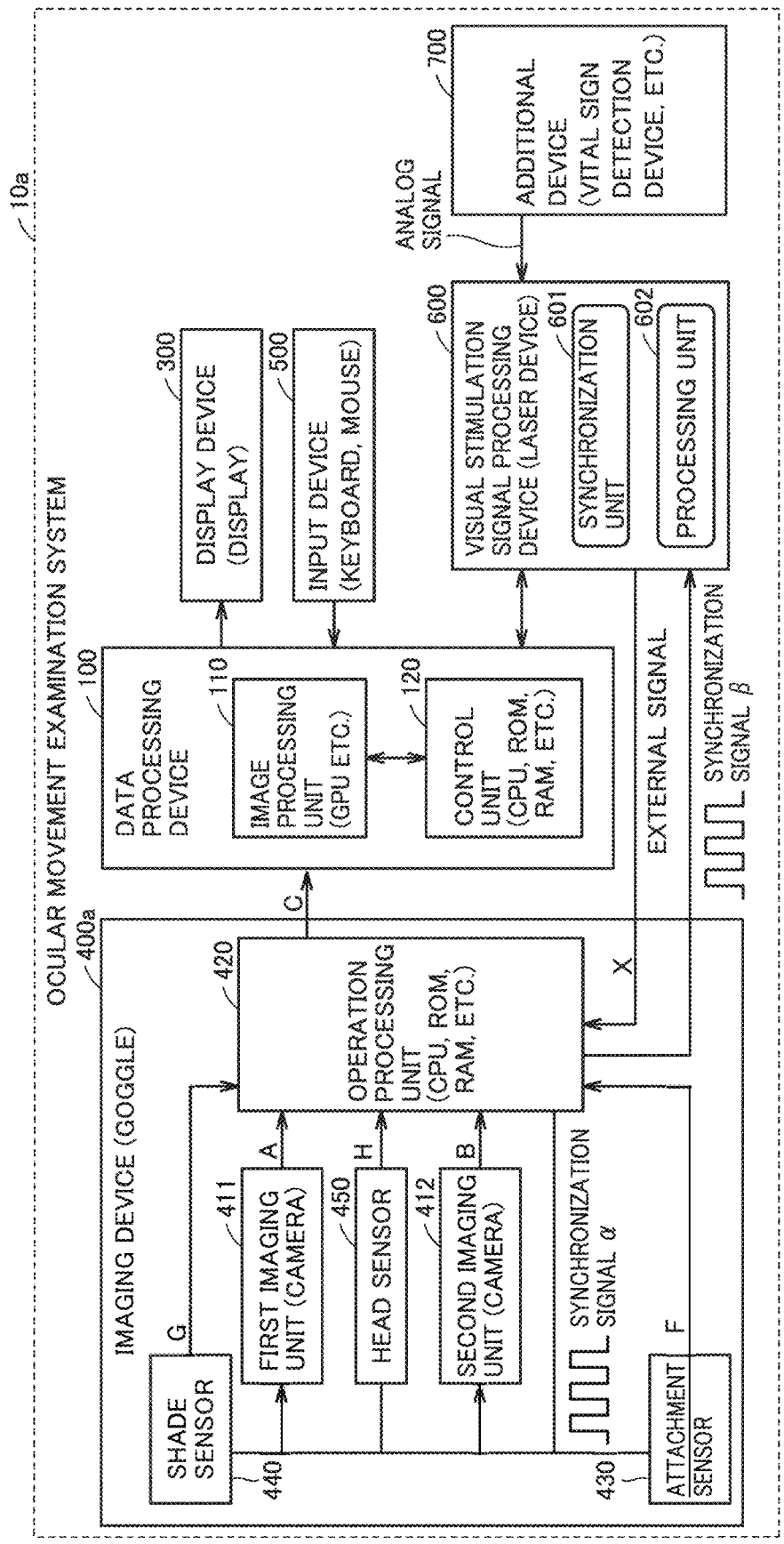
FIG. 13 is a block diagram generally showing a configuration of an ocular movement data processing system according to a second embodiment.

FIG. 13 is a block diagram generally showing a configuration of an ocular movement data processing system 10a according to the second embodiment. Ocular movement data processing system 10a shown in FIG. 13 is the same in configuration as ocular movement data processing system 10 shown in FIG. 3 except that how an imaging device 400a is configured. Accordingly, any configuration in the FIG. 13 ocular movement data processing system 10a that is identical to that of the FIG. 3 ocular movement data processing system 10 is identically denoted and will not be described specifically.

In imaging device 400a, as shown in FIG. 13, image data A from first imaging unit 411 and image data B from second imaging unit 412 are processed in operation processing unit 420 and transmitted to data processing device 100 as image data C. First imaging unit 411 includes an infrared imaging device, and a processing circuit (not shown) that attaches information of a frame number and a time stamp (first information) to an image that is captured by the infrared imaging device for each frame to provide image data A and output image data A to operation processing unit 420. The information included in the first information is not limited to a frame number and a time stamp, and may be information of at least one of the frame number and the time stamp, and may include information such as a frame rate, an amount of exposure, and a contrast. Similarly, second imaging unit 412 includes an infrared imaging device, and a processing circuit (not shown) that attaches information of a frame number and a time stamp (second information) to an image that is captured by the infrared imaging device for each frame to provide image data B and output image data B to operation processing unit 420. The information included in the second information is not limited to a frame number and a time stamp, and may be information of at least one of the frame number and the time stamp, and may include information such as a frame rate, an amount of exposure, and a contrast.

Imaging device 400a includes, in addition to first and second imaging units 411 and 412, an attachment sensor 430 that senses an attached state of housing 401 to subject 2, a shade sensor 440 that senses a shaded state of first and second imaging units 411 and 412, and a head sensor 450 that senses how subject 2 moves his/her head, how the subject orients his/her head, in particular, in housing 401. Attachment sensor 430 is, for example, a contact sensor, and when the contact sensor issues an OFF signal, operation processing unit 420 can determine that housing 401 of imaging device 400a is detached from the head of subject 2 or displaced from a prescribed position. Shade sensor 440 is, for example, an optical sensor, and when shading cover 402 is attached and imaging device 400a is internally dark, the optical sensor issues an OFF signal, and operation processing unit 420 can determine that first and second imaging units 411 and 412 are shaded. Head sensor 450 is composed of an acceleration sensor, an angular velocity sensor, and a geomagnetic sensor each provided for directions along three axes for a total of nine sensors. The acceleration sensor can sense the posture of the head of subject 2 by sensing gravitational acceleration. The angular velocity sensor can sense the angular velocity of the head of subject 2. The geomagnetic sensor can sense the orientation (or azimuth) of the head of subject 2. Operation processing unit 420 calculates head angle, head angular velocity and the like through an operation based on a measurement signal received from head sensor 450. While for imaging device 400a will be described a configuration in which attachment sensor 430, shade sensor 440, and head sensor 450 are all provided, at least one of attachment sensor 430, shade sensor 440, and head sensor 450 may be provided. As a matter of course, imaging device 400a may be provided with sensors other than attachment sensor 430, shade sensor 440, and head sensor 450.

For imaging device 400a, the signals from attachment sensor 430, shade sensor 440, and head sensor 450 are also synchronized with the images captured by first and second imaging units 411 and 412. Specifically, as a method in which imaging device 400a synchronizes an image captured by first imaging unit 411, an image captured by second imaging unit 412, and the signals received from attachment sensor 430, shade sensor 440 and head sensor 450 together, there is a method, for example, of synchronization based on time stamps added to the images and the signals received from the sensors. The time stamps are generated based on the times counted by the counters of first imaging unit 411, second imaging unit 412, attachment sensor 430, shade sensor 440, and head sensor 450, and in order to use the images and the signals received from the sensors for synchronization, it is necessary to synchronize the times counted by the counters. In order to synchronize the times counted by the counters of the imaging units and sensors, operation processing unit 420 transmits synchronization signal α to each of first imaging unit 411, second imaging unit 412, attachment sensor 430, shade sensor 440, and head sensor 450.

Based on synchronization signal α, first imaging unit 411, second imaging unit 412, attachment sensor 430, shade sensor 440, and head sensor 450 synchronize and thus adjust the time counted by each counter, and add a time stamp to each image and each sensor's signal. Based on each time stamp adjusted by synchronization signal α, operation processing unit 420 can reliably synchronize the image captured by first imaging unit 411, the image captured by second imaging unit 412, and the signals from attachment sensor 430, shade sensor 440, and head sensor 450 together to obtain a right eye image, a left eye image, and each sensor's signal of the same timing.

Operation processing unit 420 may not provide synchronization based on the time stamp added to each image and each sensor's signal, and may instead provide synchronization based on other information (e.g., a frame number, a number, etc.) added to each image and each sensor's signal. Further, operation processing unit 420 may not transmit synchronization signal α to each of first imaging unit 411, second imaging unit 412, attachment sensor 430, shade sensor 440, and head sensor 450, and, for example, may instead synchronize the time counted by each counter, as timed when each imaging unit and each sensor are powered on. Further, attachment sensor 430, shade sensor 440, and head sensor 450 may output a result of sensing to operation processing unit 420, as timed by synchronization signal α, without adding information such as a time stamp.

Figure 14:
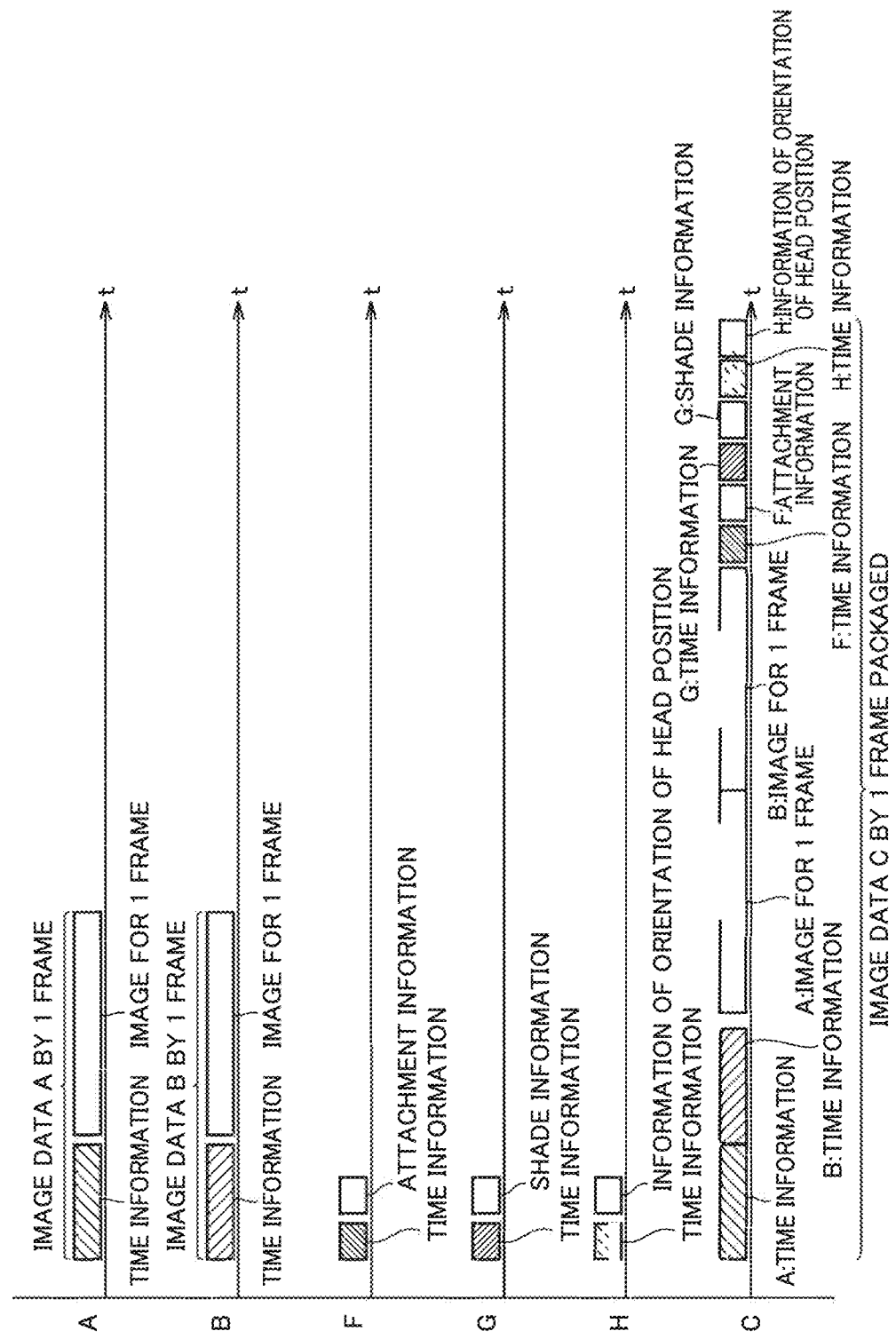
FIG. 14 is a schematic diagram representing image data of each of a first imaging unit and a second imaging unit, signals from sensors, and image data output by an operation processing unit.

Operation processing unit 420 outputs each image and each sensor's signal that are synchronized together to data processing device 100. FIG. 14 is a schematic diagram representing image data of each of first imaging unit 411 and second imaging unit 412, signals from sensors, and image data output by operation processing unit 420. As shown in FIG. 14, first imaging unit 411 adds time information (a frame number, a time stamp, etc.) to an image of one frame and outputs the image with the time information as image data A. Similarly, as shown in FIG. 14, second imaging unit 412 adds time information (a frame number, a time stamp, etc.) to an image of one frame and outputs the image with the time information as image data B.

As shown in FIG. 14, attachment sensor 430 adds time information (such as a time stamp) to attachment information (for example, an ON signal or an OFF signal) including a result of sensing, and outputs the attachment information with the time information as data F. As shown in FIG. 14, shade sensor 440 adds time information (such as a time stamp) to shade information (for example, an ON signal or an OFF signal) including a result of sensing, and outputs the shade information with the time information as data G. As shown in FIG. 14, head sensor 450 adds time information (such as a time stamp) to information of movement of the head (e.g., a measurement signal) including a result of sensing, and outputs the information with the time information as data H. As shown in FIG. 14, operation processing unit 420 processes the image of one frame of first imaging unit 411 and the image of one frame of second imaging unit 412 including the same time information as one image, and outputs the processed image, the time information of first and second imaging units 411 and 412, data F of attachment sensor 430, data G of shade sensor 440, and data H of head sensor 450 as one image data C. While FIG. 14 shows data F of attachment sensor 430, data G of shade sensor 440, and data H of head sensor 450 disposed in order after the processed image, each time information may be combined into one piece of time information, and attachment information of data F, shade information of data G, and head movement information of data H may be combined into one piece of information.

As described above, imaging device 400*a* according to the second embodiment further comprises head sensor 450 (a first detection unit) that is held by housing 401 and senses movement of the head of subject 2, and operation processing unit 420 synchronizes together first image 41 captured by first imaging unit 411, second image 42 captured by second imaging unit 412, and a result of sensing (a measurement signal) by head sensor 450. Thus, imaging device 400*a* can accurately grasp a movement of the head of subject 2 made when first and second imaging units 411 and 412 capture images, and thus allows appropriate diagnosis.

Further, the attachment sensor 430 that is held by housing 401 and senses an attached state of housing 401 is further comprised and operation processing unit 420 synchronizes together the first image captured by first imaging unit 411, the second image captured by second imaging unit 412, and a result of sensing (an ON signal or an OFF signal) by attachment sensor 430. Thus, imaging device 400*a* can accurately grasp an attached state of imaging device 400*a* made when first and second imaging units 411 and 412 capture images, and thus allows appropriate diagnosis.

Further, the shade sensor 440 that is held by housing 401 and senses a shaded state of a portion imaged by first imaging unit 411 and a shaded state of a portion imaged by second imaging unit 412 is further comprised, and operation processing unit 420 synchronizes together the first image captured by first imaging unit 411, the second image captured by second imaging unit 412, and a result of sensing (an ON signal or an OFF signal) by shade sensor 440. Thus, imaging device 400*a* can accurately grasp a shaded state of first and second imaging units 411 and 412 made when the imaging units capture images, and thus allows appropriate diagnosis.

Modified Example

In the first embodiment, imaging device 400 includes the synchronized first and second images 41 and 42 as one image in image data C and outputs image data C. However, image data C output by imaging device 400 is not limited as shown in FIG. 4, that is, to a configuration in which an image of one frame of first imaging unit 411 and an image of one frame of second imaging unit 412 including the same time information are processed as one image, and the processed image and the time information of first and second imaging units 411 and 412 are output as one image data C. For example, imaging device 400 may alternately dispose image data A of first imaging unit 411 and image data B of second imaging unit 412 including the same time information and output the same as image data C.

Figure 15:
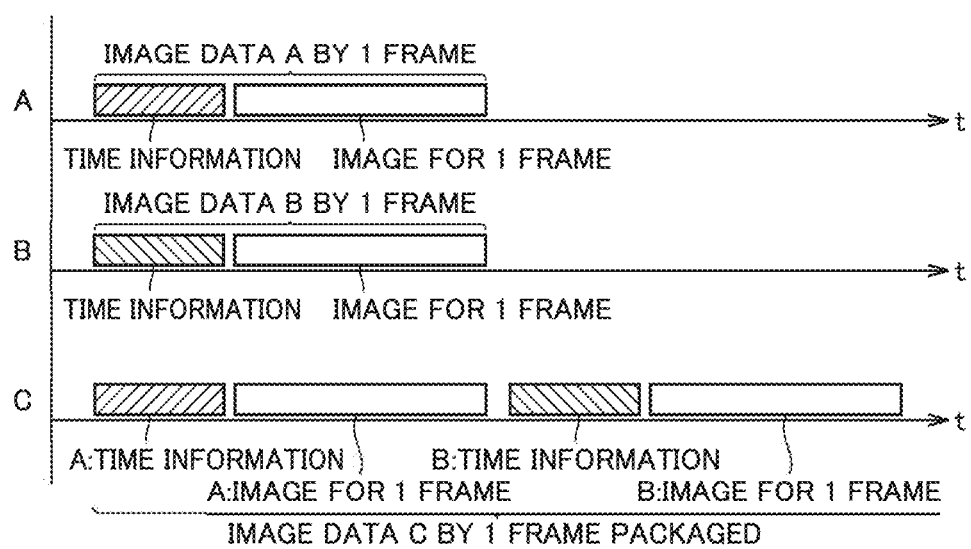
FIG. 15 is a schematic diagram for illustrating the first and second imaging units' respective images alternately disposed to output image data.

FIG. 15 is a schematic diagram for illustrating an image of first imaging unit 411 and that of second imaging unit 412 alternately disposed to output image data. As shown in FIG. 15, operation processing unit 420 alternately disposes image data A of first imaging unit 411 and image data B of second imaging unit 412 including the same time information to package them into image data C and thus outputs image data C. An image of one frame of first imaging unit 411 and an image of one frame of second imaging unit 412 including the same time information are not processed as one image; rather, image data A and image data B are simply packaged into one image data C and output. While in the example shown in FIG. 15 the time information of first imaging unit 411 and the time information of second imaging unit 412 are separately output, the time information of first imaging unit 411 and the time information of second imaging unit 412 may be combined into one and thus output.

The modified example shown in FIG. 15 is also similarly applicable to image data C output by imaging device 400*a* according to the second embodiment.

As described above, operation processing unit 420 of the modified example alternately transmits image data A and image data B with a first image and a second image synchronized together. This ensures that data processing device 100 receives the synchronized image data A and B, and providing the synchronized images to operator 1 allows an appropriate diagnosis of vertigo to be made.

Although the present embodiments have been described and illustrated in detail, it is clearly understood that the same is by way of illustration and example only and is not to be taken by way of limitation. The scope of the present invention is interpreted by the terms of the appended claims, and any modification within the meaning and scope equivalent to the terms of the claims is intended to be encompassed.

The invention claimed is:

1. An imaging device that images an eyeball in an equilibrium examination, comprising:
   a housing that is mounted on a head of a subject;
   a first camera that is held by the housing and captures a first image of a first eyeball of the subject;
   a second camera that is held by the housing and captures a second image of a second eyeball of the subject;
   first detector circuitry that is held by the housing and configured to detect a first shaded state of a first portion imaged by the first camera and a second shaded state of a second portion imaged by the second camera;
   controller circuitry held by the housing and configured to synchronize the first image captured by the first camera, the second image captured by the second camera, and a first result of detection from the first detector circuitry to process the first image and the second image into one image data in a frame package having time information included in the frame package along with the one image data; and
   communication circuitry held by the housing and configured to transmit the one image data processed by the controller circuitry to an external data processing device that performs data processing for the equilibrium examination based on the one image data.

2. The imaging device according to claim 1, wherein
the first camera outputs each captured first image, with first information added thereto, as first image data to the controller circuitry,
the second camera outputs each captured second image, with second information added thereto, as second image data to the controller circuitry,
the controller circuitry is further configured to synchronize the first image and the second image together based on the first information included in the first image data and the second information included in the second image data, and
the communication circuitry is further configured to externally transmit the first image data and the second image data, the first image data and the second image data being synchronized by the controller circuitry.

3. The imaging device according to claim 2, wherein the communication circuitry is further configured to alternately transmit the first image data and the second image data with the first image and the second image synchronized together.

4. The imaging device according to claim 2, wherein
the controller circuitry is further configured to process the first image and the second image that are synchronized as one image, and
the communication circuitry is further configured to externally transmit image data, including the one image obtained through processing by the controller circuitry, and first information and second information corresponding to the one image.

5. The imaging device according to claim 2, wherein
the controller circuitry is further configured to transmit a synchronization signal to the first camera and the second camera, and
the first camera and the second camera synchronize together the first information and the second information based on the synchronization signal.

6. The imaging device according to claim 5, wherein the synchronization signal, transmitted to the first camera and the second camera, is periodically repeated.

7. The imaging device according to claim 2, wherein the first information and the second information each at least include a timestamp.

8. The imaging device according to claim 1, further comprising second detector circuitry that is held by the housing and is configured to detect movement of the head of the subject, wherein the controller circuitry is further configured to synchronize together the first image captured by the first camera, the second image captured by the second camera, and a second result of detection by the second detector circuitry.

9. The imaging device according to claim 1, further comprising third detector circuitry that is held by the housing and configured to detect an attached state of the housing, wherein the controller circuitry is further configured to synchronize the first image captured by the first camera, the second image captured by the second camera, and a third result of detection by the third detector circuitry.

10. An ocular movement data processing system that processes ocular movement data in an equilibrium examination, comprising:
an imaging device that images an eyeball of a subject; and
a data processing device that receives data from the imaging device and processes the data,
wherein the imaging device includes:
a housing that is mounted on a head of the subject;
a first camera that is held by the housing and captures a first image of a first eyeball of the subject;
a second camera that is held by the housing and captures a second image of a second eyeball of the subject;
first detector circuitry that is held by the housing and configured to detect a first shaded state of a first portion imaged by the first camera and a second shaded state of a second portion imaged by the second camera;
controller circuitry held by the housing and configured to synchronize the first image captured by the first camera, the second image captured by the second camera, and a first result of detection from the first detector circuitry to process the first image and the second image into one image data in a frame package having time information included in the frame package along with the one image data; and
communication circuitry held by the housing and configured to transmit, to the data processing device that performs data processing for the equilibrium examination based on the one image data, the one image data processed by the controller circuitry, and
wherein the data processing device includes:
receiving circuitry configured to receive the first image and the second image from the imaging device; and
processing circuitry configured to subject the first image and second image to data processing.

11. A method for controlling implemented by an imaging device that images an eyeball in an equilibrium examination, the imaging device including: a housing that is mounted on a head of a subject, a first camera that is held by the housing and captures a first image of a first eyeball of the subject, and a second camera held by the housing and captures a second image of a second eyeball of the subject, the method comprising:
causing the first camera and the second camera to respectively image the first eyeball and the second eyeball of the subject;
detecting, by first detector circuitry held by the housing, a first shaded state of a first portion imaged by the first camera and a second shaded state of a second portion imaged by the second camera;
synchronizing, by controller circuitry held by the housing, the first image captured by the first camera, the second image captured by the second camera, and a first result of detection from the first detector circuitry to process the first image and the second image into one image data in a frame package having time information included in the frame package along with the one image data; and
externally transmitting, by communication circuitry held by the housing, the one image data to an external data processing device that performs data processing for the equilibrium examination based on the one image data.

12. The method according to claim 11, further comprising:
processing the first image and the second image that are synchronized as one image; and
externally transmitting image data, including the one image obtained through the processing, and first information and second information corresponding to the one image.

13. The method according to claim 11, further comprising:
transmitting a synchronization signal to the first camera and the second camera, and synchronizing, at the first camera and the second camera, first information and second information based on the synchronization signal.

14. The method according to claim 13, further comprising:
periodically repeating the synchronization signal transmitted to the first camera and the second camera.

15. A non-transitory computer readable medium having stored thereon a program that when executed by a computer causes the computer to implement the method for controlling implemented by the imaging device that images the eyeball in the equilibrium examination according to claim 11.

* * * * *